United States Patent
Miyazaki (10) Patent No.: US 9,819,830 B2
(45) Date of Patent: Nov. 14, 2017

(54) IMAGE FORMING APPARATUS, IMAGE FORMING SYSTEM, AND METHOD FOR FORMING IMAGES INCLUDING EXTERNAL DEVICES

(71) Applicant: KYOCERA Document Solutions Inc., Osaka-shi, Osaka (JP)

(72) Inventor: Tadashi Miyazaki, Osaka (JP)

(73) Assignee: KYOCERA DOCUMENT SOLUTIONS INC., Osaka-Shi, Osaka (JP)

(*) Notice: Subject to any disclaimer, the term of this patent is extended or adjusted under 35 U.S.C. 154(b) by 0 days.

(21) Appl. No.: 15/307,380

(22) PCT Filed: Jun. 26, 2015

(86) PCT No.: PCT/JP2015/068576
§ 371 (c)(1),
(2) Date: Oct. 28, 2016

(87) PCT Pub. No.: WO2015/199235
PCT Pub. Date: Dec. 30, 2015

(65) Prior Publication Data
US 2017/0104890 A1    Apr. 13, 2017

(30) Foreign Application Priority Data
Jun. 27, 2014  (JP) .................................. 2014-132459

(51) Int. Cl.
*G06F 3/12*    (2006.01)
*H04N 1/00*    (2006.01)
(Continued)

(52) U.S. Cl.
CPC ............... *H04N 1/442* (2013.01); *A61B 5/01* (2013.01); *A61B 5/0245* (2013.01);
(Continued)

(58) Field of Classification Search
CPC ..... A61B 5/01; A61B 5/02055; A61B 5/0245; A61B 5/117; A61B 5/16; A61B 5/4266;
(Continued)

(56) References Cited

U.S. PATENT DOCUMENTS 6,280,105 B1    8/2001  Iida
7,812,986 B2 *  10/2010 Graham ................. G06K 9/325
                                                        358/1.15
(Continued)

FOREIGN PATENT DOCUMENTS

JP    H10304217 A    11/1998
JP    2000190573 A    7/2000
(Continued)

*Primary Examiner* — Gabriel Garcia (57) ABSTRACT

An image forming apparatus (100) includes a biological information acquiring unit (402) that, upon accepting a print job transmitted by a user through a preset terminal device (103), identifies the terminal device (103) including a biological information detecting unit based on the terminal device's (103) identification information assigned to the print job, and acquires the user's biological information detected by the biological information detecting unit through a biological information receiving unit, a biological information determining unit (403) that determines whether or not the acquired biological information corresponds to reference biological information indicating that the user is in a hurry, and a calibration control unit (404) that, if the determination result shows that the acquired biological information corresponds to the reference biological information, disables regularly scheduled calibration at a time of, or during execution of the accepted print job.

4 Claims, 7 Drawing Sheets

(51) Int. Cl.
    *H04N 1/44*     (2006.01)
    *A61B 5/01*     (2006.01)
    *A61B 5/0245*     (2006.01)
    *A61B 5/16*     (2006.01)
    *B41J 2/525*     (2006.01)
    *B41J 29/00*     (2006.01)
    *B41J 29/38*     (2006.01)
    *G03G 21/00*     (2006.01)
    *G06F 3/01*     (2006.01)
    *A61B 5/0205*     (2006.01)
    *A61B 5/117*     (2016.01)
    *A61B 5/00*     (2006.01)

(52) U.S. Cl.
    CPC .......... *A61B 5/02055* (2013.01); *A61B 5/117* (2013.01); *A61B 5/16* (2013.01); *A61B 5/4266* (2013.01); *B41J 2/525* (2013.01); *B41J 29/00* (2013.01); *B41J 29/38* (2013.01); *G03G 21/00* (2013.01); *G06F 3/01* (2013.01); *G06F 3/12* (2013.01); *H04N 1/00* (2013.01); *H04N 1/4426* (2013.01); *H04N 2201/0094* (2013.01)

(58) Field of Classification Search
    CPC . B41J 2/525; B41J 29/00; B41J 29/38; G03G 21/00; G06F 3/01; G06F 3/12; H04N 1/00; H04N 1/442; H04N 1/4426; H04N 2201/094
    USPC .................................................. 358/1.1–1.18
    See application file for complete search history.

(56) References Cited

U.S. PATENT DOCUMENTS

| | | | |
|---|---|---|---|
| 8,493,582 B2* | 7/2013 | Murakami | G06F 21/608 358/1.13 |
| 2005/0277168 A1* | 12/2005 | Wood | G01N 15/1475 435/30 |
| 2007/0052997 A1* | 3/2007 | Hull | G06K 9/00463 358/1.15 |
| 2011/0317215 A1* | 12/2011 | Ida | G06F 3/1222 358/1.15 |
| 2016/0248926 A1* | 8/2016 | Yasuda | H04N 1/00307 |
| 2016/0352969 A1* | 12/2016 | Mashimo | H04N 1/442 |

FOREIGN PATENT DOCUMENTS

| | | |
|---|---|---|
| JP | 2005132030 A | 5/2005 |
| JP | 2006062279 A | 3/2006 |
| JP | 2006293141 A | 10/2006 |
| JP | 2008526367 A | 7/2008 |
| WO | 2006074307 A2 | 7/2006 |

* cited by examiner

FIG.6B

IMAGE FORMING APPARATUS, IMAGE FORMING SYSTEM, AND METHOD FOR FORMING IMAGES INCLUDING EXTERNAL DEVICES

RELATED APPLICATIONS

The present application is a national stage entry according to 35 U.S.C. §371 of PCT application No.: PCT/JP2015/068576 filed on Jun. 26, 2015, which claims priority from Japanese application No.: 2014-132459 filed on Jun. 27, 2014 and is incorporated herein by reference in its entirety.

TECHNICAL FIELD

This invention relates to image forming apparatuses, image forming systems, and methods for forming images, and more specifically to an image forming apparatus capable of providing improved convenience for users who need to print out an image in a hurry, an image forming system including the image forming apparatus, and a method for forming images with the image forming system.

BACKGROUND ART

Some recently image forming apparatuses, including copiers, printers, multifunction peripherals, perform calibration at predetermined times in order to maintain image quality of printed matter. Heretofore there have been various kinds of calibration techniques. For example, Japanese Unexamined Patent Application Publication No. H10 (1998)-304217 (PTL 1) discloses an image processing apparatus that when calibration is needed in the process of continuous printing, suspends the printing operation to perform calibration and resumes the printing operation afterward. Japanese Unexamined Patent Application Publication No. 2000-190573 (PTL 2) discloses a print system that does not perform calibration if the system determines that a print job includes a calibration stop command.

Japanese Unexamined Patent Application Publication No. 2005-132030 (PTL 3) discloses a color printing apparatus that performs calibration concurrently with print data processing, but aborts the calibration if it is unnecessary. Japanese Unexamined Patent Application Publication No. 2006-62279 (PTL 4) discloses an image forming apparatus that when receiving a print command during calibration, allows users to selectively assign priority to the calibration or the print command. In addition, Japanese Unexamined Patent Application Publication No. 2006-293141 (PTL 5) discloses an image forming apparatus that sets an optimal toner ejection mode to be used in a refresh process performed to refresh toner on a developing roller according to users' usage.

By the way, recent technological advances have developed apparatuses for measuring users' biological signals. For example, Japanese Translation of PCT International Application Publication No. 2008-526367 (PTL 6) discloses a portable vital signs measurement instrument that provides a variety of measurement capabilities to indicate patient conditions, such as blood pressure, temperature, and pulse oximetry.

CITATION LIST

Patent Literature

PTL1: JP-A-H10(1998)-304217
PTL2: JP-A-2000-190573
PTL3: JP-A-2005-132030
PTL4: JP-A-2006-62279
PTL5: JP-A-2006-293141
PTL6: JP-T-2008-526367

SUMMARY OF INVENTION

Technical Problem

Some image forming apparatuses are set to regularly and automatically calibrate and refresh themselves, under conditions, for example, the cumulative number of printed sheets, the period of printing time, or at the time of power-on.

The technique disclosed in PTL 1 lowers the productivity of the entire print job because calibration is performed during the continuous printing operation, and therefore may significantly impair the convenience of users who want to have the printing job done quickly. The technique disclosed in PTL 2 requires users to add the calibration stop command to the print job, which is a time and effort consuming task.

The techniques disclosed in PTLs 3 to 5 determine whether or not to perform calibration in response to key operations by users. For users in a hurry, the key operations are burdensome, thereby impairing users' convenience.

The present invention has been made to solve the aforementioned problems and has an object of providing an image forming apparatus capable of providing improved convenience for users who need to print out an image in a hurry, an image forming system including the image forming apparatus, and a method for forming images with the image forming system.

Solution to Problem

In order to solve the aforementioned problems and achieve the object, the image forming apparatus according to the present invention includes a biological information acquiring unit, a biological information determining unit, and a calibration control unit. Upon accepting a print job transmitted by a user through a preset terminal device, the biological information acquiring unit identifies the terminal device including a biological information detecting unit based on the identification information for terminal device assigned to the print job, and acquires the user's biological information detected by the biological information detecting unit through a biological information receiving unit. The biological information determining unit determines whether or not the acquired biological information corresponds to reference biological information indicating that the user is in a hurry. If the determination result shows that the acquired biological information corresponds to the reference biological information, the calibration control unit disables regularly scheduled calibration at a time of, or during execution of the accepted print job.

The present invention also directs to an image forming system including an image forming apparatus, a first terminal device capable of communicating with the image forming apparatus, and a second terminal device capable of communicating with the first terminal device. The second terminal device includes a biological information detecting unit that detects a user's biological information, the first terminal device includes a biological information receiving unit that receives the user's biological information detected by the biological information detecting unit, and a biological information acquiring unit that acquires the biological information received by the biological information receiving unit. The image forming apparatus or the first terminal device includes a biological information determining unit that determines whether or not the acquired biological information corresponds to reference biological information indicating that the user is in a hurry. Upon accepting a print job from the second terminal device, the first terminal device identifies the second terminal device including the biological information detecting unit based on the second identification information for terminal device assigned to the print job, and acquires the biological information received by the biological information receiving unit of the second terminal device through the biological information acquiring unit. The biological information determining unit determines whether or not the acquired biological information corresponds to the reference biological information indicating that the user is in a hurry. The image forming apparatus includes a calibration control unit that, if the determination result shows that the acquired biological information corresponds to the reference biological information, disables regularly scheduled calibration at a time of, or during execution of the accepted print job.

The present invention can be provided as a method for forming images. Specifically, the image forming method according to the invention includes the steps of, upon accepting a print job transmitted by a user through a preset terminal device, identifying the terminal device including a biological information detecting unit based on the identification information for terminal device assigned to the print job, and acquiring the user's biological information detected by the biological information detecting unit through a biological information receiving unit. The method also includes the step of determining whether or not the acquired biological information corresponds to reference biological information indicating that the user is in a hurry. The method still includes the step of, if the determination result shows that the acquired biological information corresponds to the reference biological information, disabling regularly scheduled calibration at a time of, or during execution of the accepted print job. Such a configuration can also offer the same effects as above.

Advantageous Effect of Invention

The image forming apparatus, the image forming system, and the image forming method according to the present invention can provide improved convenience for users who need to print images in a hurry.

DESCRIPTION OF EMBODIMENT

With reference to the accompanying drawings, embodiments of the present invention will be described for further understanding of the invention. It should be noted that the present embodiments are mere examples of implementation of the present invention, and in no way restrict the technical scope of the present invention. The alphabetic script "S" attached before a numeral in the flowchart means "step".

A description will be made below about an image forming apparatus as an example of the embodiments of the invention. The image forming apparatus of the invention corresponds to, for example, a multifunction peripheral (MFP) having the functions of a copier, a scanner, a printer and so on.

Figure 1:
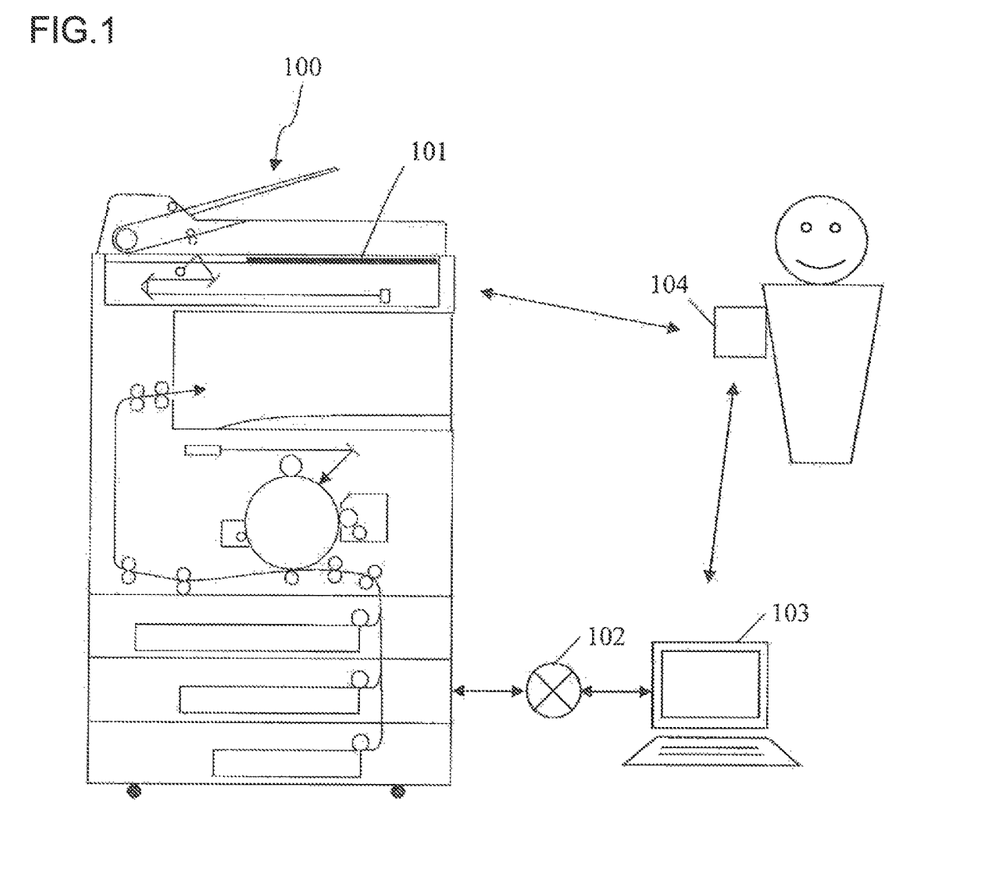
FIG. 1 is a schematic diagram of a multifunction peripheral according to an embodiment of the present invention.

As shown in FIG. 1, the MFP 100 accepts the setting conditions of a print job from a user through an operation unit 101, and actuates various units (an image reading unit, an image forming unit, a transport unit, a fusing unit, etc.) to provide the print job.

The MFP 100 is communicably connected to a terminal device 103 (PC or the like) through a network 102 to receive print jobs created by the terminal device 103 and to provide the print jobs.

A user carries a biological information processing device 104 that detects the user's biological information (e.g., heart rate, temperature, perspiration level, electrocardiogram, etc.) and transmits the information to the MFP 100 or the terminal device 103. The MFP 100 or the terminal device 103 includes a receiver that receives the biological information transmitted from the biological information processing device 104. The biological information processing device 104 is a portable terminal device equipped with, for example, a biological information detection unit (which is a sensor, such as a heart-beat sensor, and a high performance sensor). A portable terminal device 104 communicates with the MFP 100 or the terminal device 103 wirelessly via, for example, a WLAN or Bluetooth (registered trademark).

Figure 2:
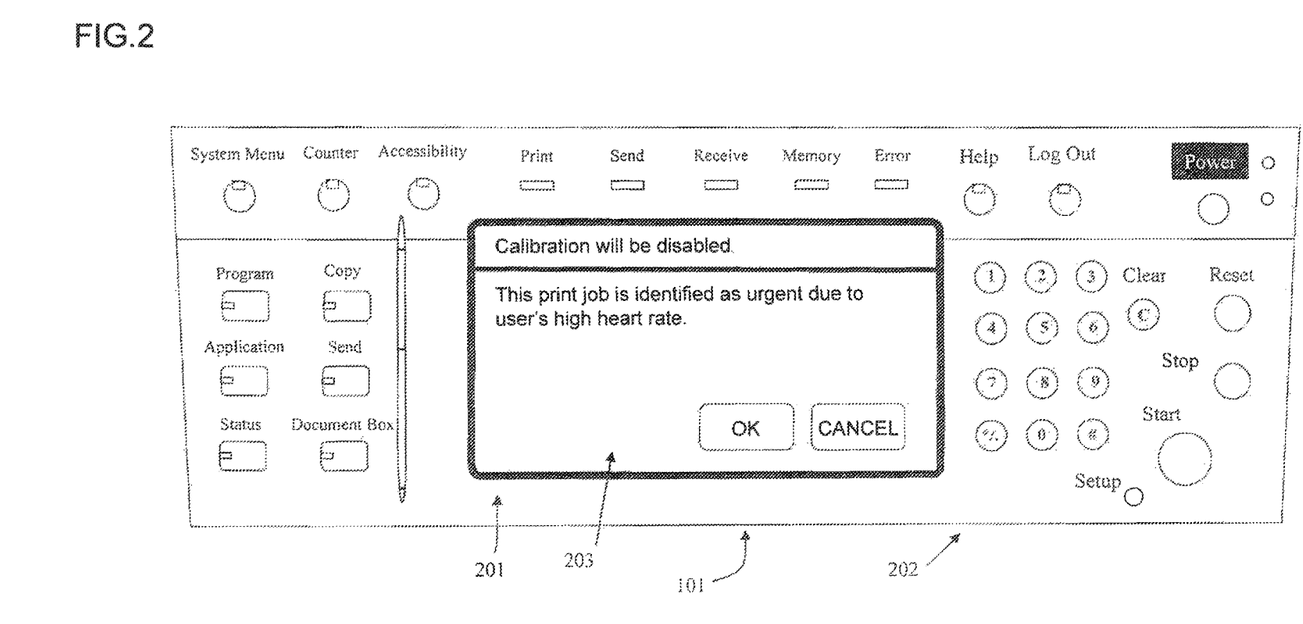
FIG. 2 is a conceptual view illustrating the overall configuration of an operation unit according to the embodiment of the invention.

With reference to FIG. 2, the configuration of the operation unit 101 will be described. As shown in FIG. 2, the operation unit 101 includes a touch panel 201 (operation panel) and an operation key set 202, and is used by the user to input specific instructions and check predetermined operation screens through the operation unit 101. The touch panel 201 displays predetermined screens, and allows the user to input information by depressing keys on the displayed screen associated with the information. The operation key set 202 includes, for example, a numeric keypad, a start key, a clear key, a stop key, a reset key, a power key, etc.

Figure 3:
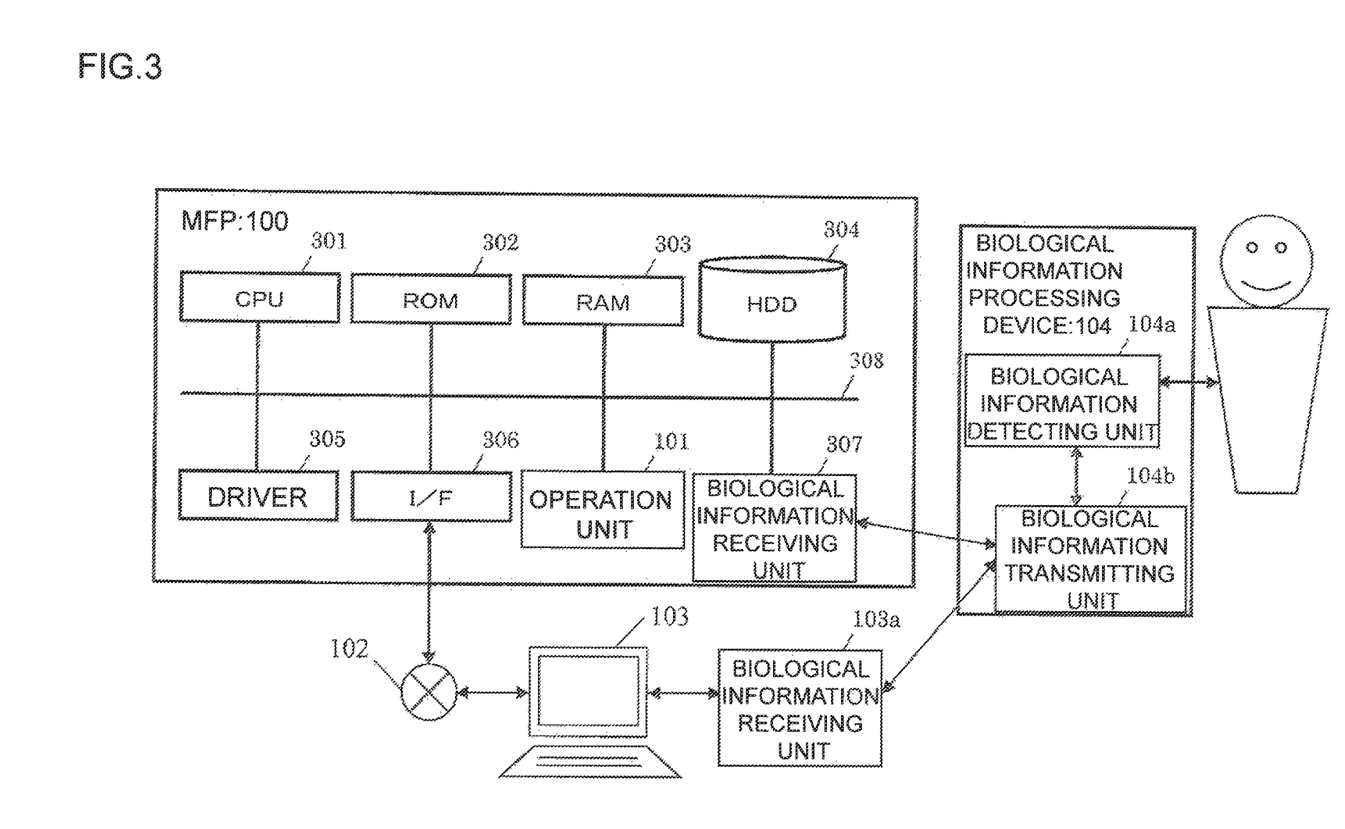
FIG. 3 shows the configuration of control system hardware in the multifunction peripheral according to the embodiment of the invention.

With reference to FIG. 3, a description will be made about the configuration of control system hardware in the MFP 100. As shown in FIG. 3, a control circuit of the MFP 100 is composed of a central processing unit (CPU) 301, a read only memory (ROM) 302, a random access memory (RAM) 303, a hard disk drive (HDD) 304, a driver 305 associated with each driving unit, an external interface (I/F) 306, the operation unit 101, and a biological information receiving unit 307, all of which are connected to one another by an internal bus 308. The terminal device 103 is connected to the MFP 100 via a network 102 and includes a control circuit (CPU, ROM, RAM, HDD, etc.) (not shown) and a biological information receiving unit 103a.

The portable terminal device 104 carried by the user includes a biological information detecting unit 104a and a biological information transmitting unit 104b. The biological information transmitting unit 104b transmits the biological information of the user to the biological information receiving unit 307 of the MFP 100 or the biological information receiving unit 103a of the terminal device 103.

The CPU of MFP 100 or the CPU of the terminal device 103, for example, uses the RAM as a work area, executes programs stored in the ROM, HDD, or other storages, and receives data, instructions, signals, or commands from the driver, operation unit 101, or biological information receiving unit 307 or 103a based on the execution results of the programs in order to control the operation of each drive unit shown in FIG. 1. Other units (shown in FIGS. 4A and 4B) described hereafter, except for the aforementioned drive unit, are also operated by the CPU that executes the programs. The programs and data for implementing each unit described below are stored in the ROM, RAM, HDD or other storage units.

Next, with reference to FIGS. 4A, 4B, and 5, a description will be given about the configuration and execution procedure according to embodiments of the present invention.

<A Case where a Biological Information Receiving Unit is Provided in an Image Forming Apparatus>

Figure 4A:
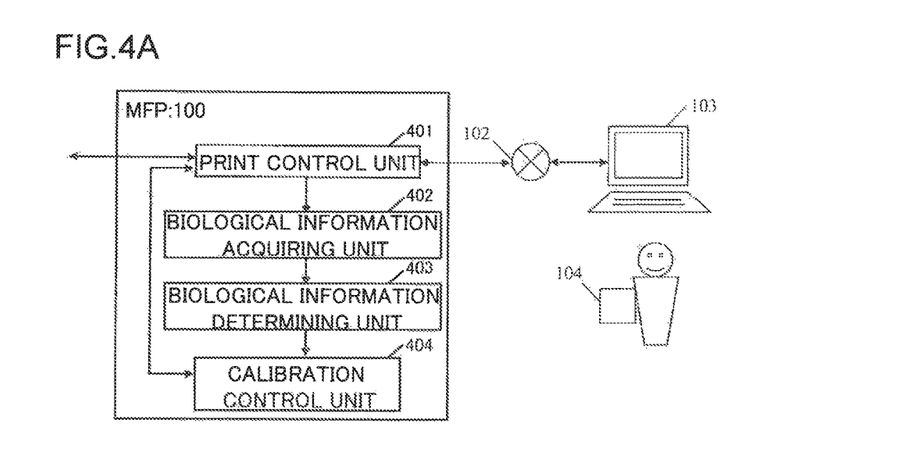
FIG. 4A is a functional block diagram of a multifunction peripheral and a terminal device according to the first embodiment of the invention.
Figure 6A:
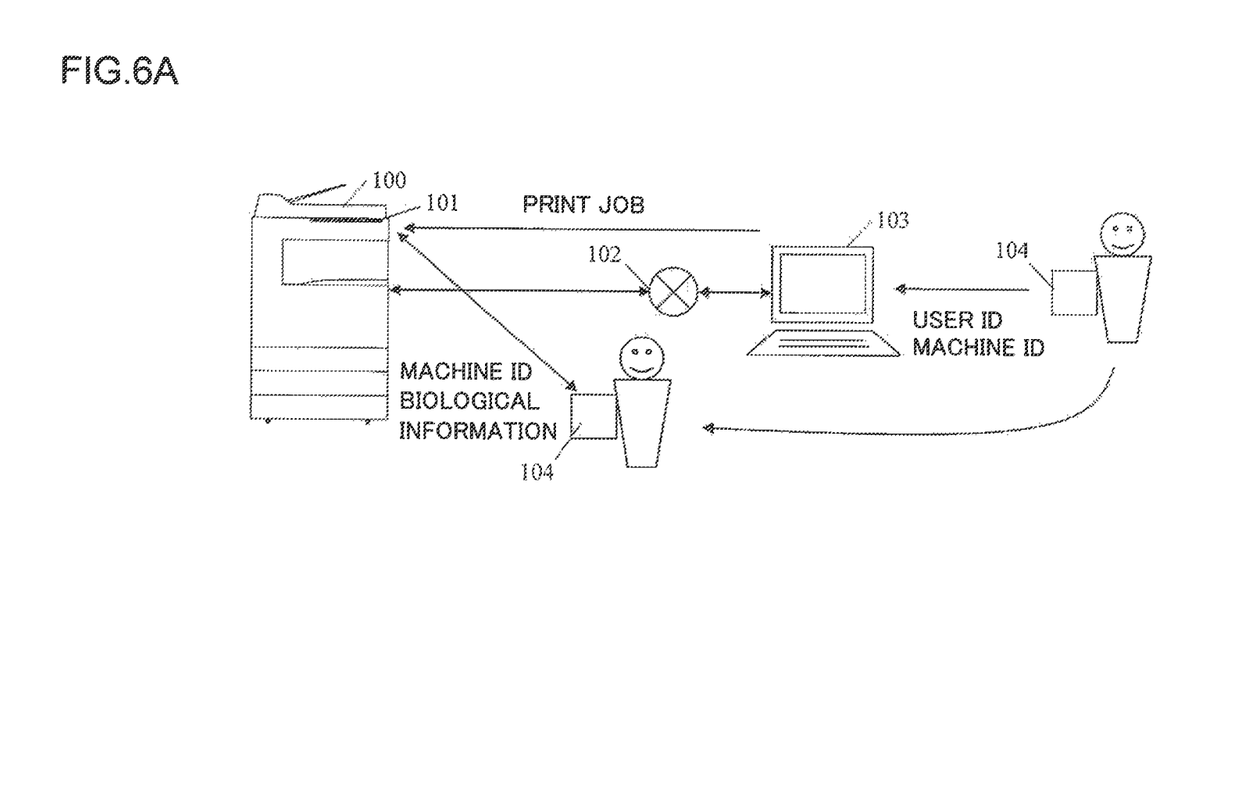
FIG. 6A shows the relationship among the multifunction peripheral, the terminal device, and a portable terminal device of a user according to the first embodiment of the invention.

Firstly, as shown in FIGS. 4A and 6A, a user carrying the portable terminal device 104 creates a print job using the terminal device 103. The created print job is assigned with identification information of the user (user ID, e.g., "AAA") and the identification information of the portable terminal device 104 (or the biological information detecting unit 104a of the portable terminal device 104) (machine ID corresponding to IP address or the like, e.g., "BBB").

Figure 5:
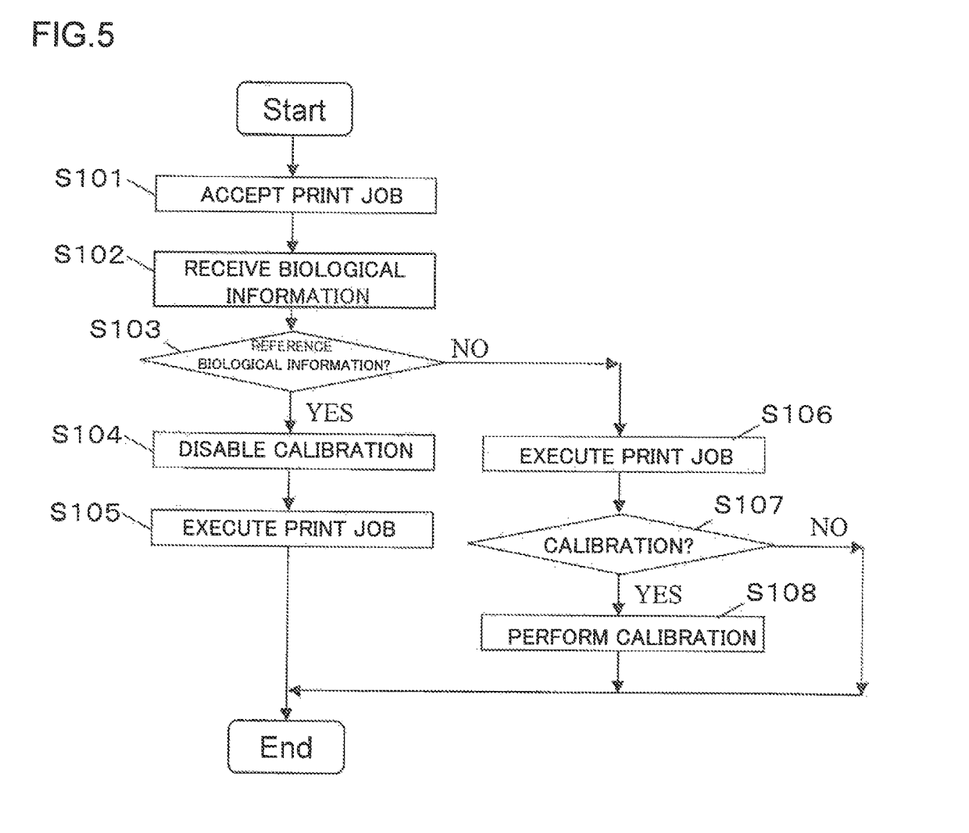
FIG. 5 is a flow chart describing an execution procedure according to the embodiments of the invention.

When the user transmits the created print job from the terminal device 103 to the MFP 100 via the network 102, a print control unit 401 of the MFP 100 accepts the print job (FIG. 5: S101).

After accepting the print job, the print control unit 401 notifies a biological information acquiring unit 402 of the acceptance. The biological information acquiring unit 402 that has received the notification identifies the portable terminal device 104 having the biological information detecting unit 104a based on machine ID "BBB" assigned to the print job, and acquires the user's biological information (e.g., heart rate) detected (monitored) by the biological information detecting unit 104a through the biological information receiving unit 307 (FIG. 5: S102). In this case, the MFP 100 acquires the biological information.

The method by which the biological information acquiring unit 402 acquires the information is not particularly limited. For example, the biological information acquiring unit 402 activates the biological information receiving unit 307 to acquire machine IDs of terminal devices within the communicable range of the biological information receiving unit 307, and compares the acquired machine IDs with machine ID "BBB" assigned to the print job to detect whether one of the terminal devices in the communicable range of the biological information receiving unit 307 is user's the portable terminal device 104.

If the user comes to the MFP 100 immediately after transmitting the print job to the MFP 100 as shown in FIG. 6A, the biological information acquiring unit 402 of the MFP 100 detects that user's the portable terminal device 104 exists, and acquires the user's biological information (heart rate) from the biological information detecting unit 104a through the biological information transmitting unit 104b of the portable terminal device 104.

In the case where the biological information detecting unit 104a has been already activated and has detected the user's biological information, the biological information acquiring unit 402 acquires the user's biological information through the biological information transmitting unit 104b. On the other hand, in the case where the biological information detecting unit 104a has not been activated, the biological information acquiring unit 402 activates the biological information detecting unit 104a to acquire the user's biological information from the biological information detecting unit 104a.

Upon acquiring the biological information, the biological information acquiring unit 402 notifies a biological information determining unit 403 of the information acquisition. The biological information determining unit 403 that has received the notification determines whether the acquired biological information corresponds to reference biological information indicating that the user is in a hurry (FIG. 5: S103).

The method by which the biological information determining unit 403 makes determination is not particularly limited. For example, in the case where the biological information is the user's heart rate, which becomes higher when the user is in a hurry, a heart rate close to heart rates obtained from users who are in a hurry is set in the reference biological information as a threshold value, and the biological information determining unit 403 determines whether the acquired heart rate is higher or not higher than the threshold value. If the acquired heart rate is determined to be higher than the threshold value, the biological information determining unit 403 determines that the acquired biological information corresponds to the reference biological information, while if the acquired heart rate is equal to or lower than the threshold value, the biological information determining unit 403 determines that the acquired biological information does not correspond to the reference biological information.

Additionally, in the case where the biological information denotes a heart rate that tends to drastically vary over time, for example, the time-varying heart-rate changes (distributions) when users are in a hurry are converted into a pattern and the pattern is set into the reference biological information, and the biological information determining unit 403 determines whether the acquired heart rate corresponds to the pattern. If the acquired heart rate corresponds to (or is equivalent to) the pattern, the biological information determining unit 403 determines that the acquired biological information corresponds to the reference biological information, while if the acquired heart rate does not correspond to the pattern, the biological information determining unit 403 determines that the acquired biological information does not correspond to the reference biological information. It is also possible to configure the biological information determining unit 403 so as to obtain an average value of the user's heart rates from the pattern and determine whether the average value is higher or not higher than the threshold value.

The point in time at which the biological information determining unit 403 makes determination is not particularly limited, and the biological information determining unit 403 can make determination at the time of the acceptance of a print job as described above, or during the execution of the print job.

If the determination results shows that the acquired biological information corresponds to the reference biological information in S103 (FIG. 5: YES in S103), the biological information determining unit 403 determines that the user who has transmitted the print job is in a hurry and notifies a calibration control unit 404 of the determination. The calibration control unit 404 receives the notification and disables regularly scheduled calibration to perform the accepted print job (FIG. 5: S104).

The aforementioned calibration means operations to improve image quality of printed matter and includes, for example, color registration processing, color adjustment processing, refresh operation for ejecting old toner, correction of development conditions, etc. This calibration takes from one minute to several minutes.

The method for disabling the calibration control unit 404 is not particularly limited. For example, if the time to execute calibration comes just when the print control unit 401 receives and executes the print job and calibration is actually being performed, the calibration control unit 404 interrupts the calibration in progress to execute the print job at the highest priority (FIG. 5: S105). Thus, the user who needs to finish the print job in a hurry can cancel calibration without operating keys to input the job's urgency to the MFP 100, thereby improving the user's convenience. This is especially advantageous when users who are in a hurry give priority to printing speed.

When the calibration control unit 404 interrupts the calibration in progress, the touch panel 201 may display a notification screen 203 to notify the user that the calibration will be disabled as shown in FIG. 2.

Also when the calibration control unit 404 interrupts the calibration in progress, the calibration control unit 404 controls the print control unit 401 to resume the interrupted calibration after the print control unit 401 completes the print job. This can improve the image quality of printed matter created by the following users.

In the case where the time at which the print control unit 401 is about to a time of executing the print job is close to the time to execute calibration, the calibration control unit 404 controls the print control unit 401 to continue executing the print job (FIG. 5: S105) and disables calibration even if the time to execute calibration comes. When the print control unit 401 completes the print job, the calibration control unit 404 controls the print control unit 401 to resume the disabled calibration.

The time to execute calibration comes, for example, when a cumulative value, such as the current cumulative number of printed sheets and the cumulative print time, exceeds a predetermined threshold, or at the time of power-on.

If, in S103, the determination result shows that the acquired biological information does not correspond to the reference biological information (FIG. 5: NO in S103), the biological information determining unit 403 determines that the user who has transmitted the print job is not in a hurry, and nothing special is done. In this case, the print control unit 401 is to execute the print job (FIG. 5: S106), but the print control unit 401 also determines whether or not the time to execute calibration will come at the starting time of the print job or during execution of the print job (FIG. 5: S107). If the time to execute calibration comes (FIG. 5: YES in S107), the print control unit 401 interrupts the print job before being processed or currently being processed to execute calibration at the highest priority (FIG. 5: S108). On the other hand, if the time to execute calibration does not come (FIG. 5: NO in S107), the print control unit 401 executes only the print job without executing calibration.

<A Case where a Biological Information Receiving Unit is Provided in a Terminal Device>

Figure 4B:
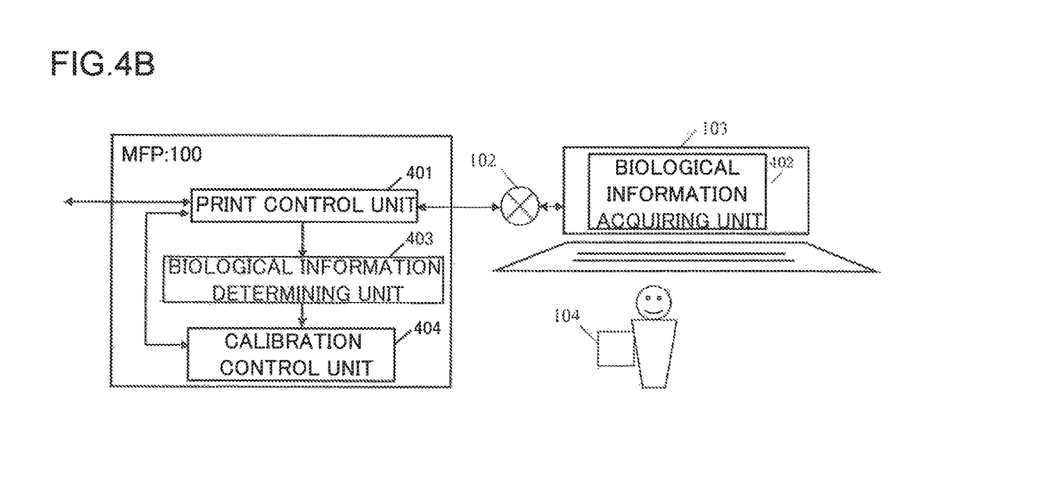
FIG. 4B is a functional block diagram of a multifunction peripheral and a terminal device according to the second embodiment of the invention.
Figure 6B:
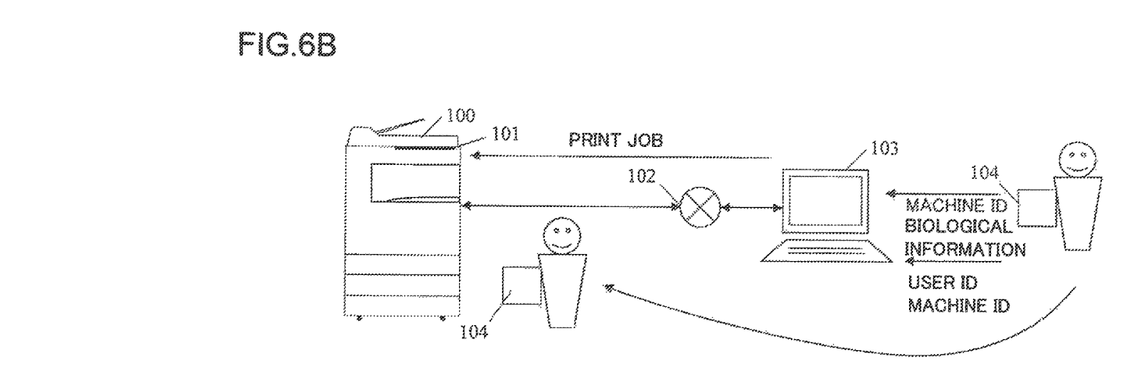
FIG. 6B shows the relationship among the multifunction peripheral, the terminal device, and a portable terminal device of a user according to the second embodiment of the invention.

Firstly, as shown in FIGS. 4B and 6B, a user carrying a portable terminal device 104 (a second terminal device) creates a print job assigned with a user ID and a machine ID using a terminal device 103 (a first terminal device), and transmits the created print job to a MFP 100. The terminal device 103 accepts the print job (FIG. 5: S101), and notifies a biological information acquiring unit 402 of the acceptance of the print job. Upon acceptance of the notification, the biological information acquiring unit 402 identifies the portable terminal device 104 having a biological information detecting unit 104a based on the machine ID "BBB" assigned to the print job, and acquires biological information from the biological information detecting unit 104a through a biological information receiving unit 103a (FIG. 5: S102). In this case, the terminal device 103 acquires the biological information. For example, a print driver installed in the terminal device 103 functions as the biological information acquiring unit 402.

The biological information acquired by the biological information acquiring unit 402 is assigned to the print job. The terminal device 103 transmits the print job to the MFP 100. The print control unit 401 accepts the print job and notifies a biological information determining unit 403 of the acceptance of the print job. The biological information determining unit 403 having received the notification determines whether the acquired biological information corresponds to reference biological information (FIG. 5: S103).

If the determination result shows that the acquired biological information corresponds to the reference biological information (FIG. 5: YES in S103), the calibration control unit 404 disables regularly scheduled calibration when the print control unit 401 executes the accepted print job (FIG. 5: S104). On the other hand, if the determination result shows that the acquired biological information does not correspond to the reference biological information (FIG. 5: NO in S103), the print control unit 401 executes the print job in the usual way (FIG. 5: S106). The image forming apparatus configured as described above produces the effects of the present invention.

Although the biological information determining unit 403 is provided in the MFP 100 in the embodiments of the present invention, it can be provided in the terminal device 103. For example, the terminal device 103 accepts a print job (FIG. 5: S101), and the biological information acquiring unit 402 acquires biological information from the biological information detecting unit 104a using the biological information receiving unit 103a (FIG. 5: S102). Then, the biological information determining unit 403 determines whether the acquired biological information corresponds to reference biological information (FIG. 5: S103). In this case, for example, a print driver installed in the terminal device 103 functions as the biological information determining unit 403.

The biological information determining unit 403 can make determination at any point in time from when the print job is accepted to during execution of the print job. For example, when the firstly acquired biological information does not correspond to the reference biological information (FIG. 5: NO in S103), the calibration control unit 404 does not work. However, if the biological information changes to correspond to the reference biological information for some reasons while the user is around the terminal device 104 (if the user's heart rate suddenly rises), the biological information determining unit 403 determines that the acquired biological information corresponds to the reference biological information (FIG. 5: YES in S103), and notifies the calibration control unit 404 of the determination as an urgent flag. Upon receipt of the notification, the calibration control unit 404 disables the regularly scheduled calibration (FIG. 5: S104). The image forming apparatus configured as described above also produces the effects of the present invention.

Although the MFP 100 and terminal device 103 in the embodiments of the invention are configured to include various units, it is also possible to provide a storage medium that stores a program for implementing the various units. To achieve the configuration, the image forming apparatus and terminal device are configured to read out the program to implement the respective units. In this case, the program itself that is read out of the storage medium may embody the operation and effects of the present invention. Furthermore, the operation steps executed by the units can be provided in the form of a method stored in a hard disk.

INDUSTRIAL APPLICABILITY

The image forming apparatus, image forming system and image forming method according to the present invention described above are useful for, not only multifunction peripherals, but also copiers, printers, terminal devices, tablet terminal devices, laptop personal computers, portable terminal devices, and other types of terminal devices, and are effective to provide improved convenience for users who need to print images in a hurry.

What is claimed is:

1. An image forming apparatus comprising:
a central processing unit for controlling the image forming apparatus, wherein
the central processing unit executes a biological information acquiring unit that, upon accepting a print job transmitted by a user through a preset terminal device, identifies the terminal device including a biological information detecting unit based on the identification information for terminal device assigned to the print job, and acquires the user's biological information detected by the biological information detecting unit through a biological information receiving unit,
wherein the biological information receiving unit acquire machine IDs of terminal devices within the communicable range of the biological information receiving unit for comparing the acquired machine IDs of terminal devices with the assigned print job;
a biological information determining unit that determines whether or not the acquired biological information corresponds to reference biological information indicating that the user is in a hurry; and
a calibration control unit that, if the determination result shows that the acquired biological information corresponds to the reference biological information, disables regularly scheduled calibration at a time of executing the accepted print job, or during execution of the accepted print job,
wherein the biological information includes the user's heart rate, temperature, perspiration level.

2. An image forming system comprising an image forming apparatus, a first terminal device capable of communicating with the image forming apparatus, and a second terminal device capable of communicating with the first terminal device, wherein the second terminal device includes a biological information detecting unit that detects a user's biological information,
the biological information includes the user's heart rate, temperature, perspiration level, and the biological information detecting unit monitors the biological information,
the first terminal device includes a biological information receiving unit that receives the user's biological information detected by the biological information detecting unit, and a biological information acquiring unit that acquires the biological information received by the biological information receiving unit,
the image forming apparatus or the first terminal device includes a biological information determining unit that determines whether or not the acquired biological information corresponds to reference biological information indicating that the user is in a hurry,
upon accepting a print job from the second terminal device, the first terminal device identifies the second terminal device based on the second identification information for terminal device assigned to the print job, and acquires the biological information received by the biological information receiving unit of the second terminal device through the biological information acquiring unit,
the biological information determining unit determines whether or not the acquired biological information corresponds to the reference biological information indicating that the user is in a hurry, and
the image forming apparatus includes a calibration control unit that, if the determination result shows that the acquired biological information corresponds to the reference biological information, disables regularly scheduled calibration at a time of executing the accepted print job, or during execution of the accepted print job.

3. The image forming system according to claim 2, wherein
the first terminal device includes a print driver installed therein, the print driver notifies the image forming apparatus or the first terminal device of the biological information with a print request, and the biological information determining unit determines whether or not the user is in a hurry based on the notified biological information.

4. A method for forming images comprising the steps of:
upon accepting a print job transmitted by a user through a preset terminal device, identifying the terminal device including a biological information detecting unit based on the identification information for terminal device assigned to the print job, and acquiring the user's biological information detected by the biological information detecting unit through a biological information receiving unit;
determining whether or not the acquired biological information corresponds to reference biological information indicating that the user is in a hurry; and
if the determination result shows that the acquired biological information corresponds to the reference biological information, disabling regularly scheduled calibration at a time of executing the accepted print job, or during execution of the accepted print job,
wherein the biological information includes the user's heart rate, temperature, perspiration level.

* * * * *